(12) United States Patent
Akyuz et al.

(10) Patent No.: US 8,728,162 B2
(45) Date of Patent: May 20, 2014

(54) DIRECT LATERAL SPINE SYSTEM INSTRUMENTS, IMPLANTS AND ASSOCIATED METHODS

(75) Inventors: Ephraim Akyuz, Logan, UT (US); Andrew Fauth, River Heights, UT (US); Douglas M. Lorang, North Logan, UT (US); Daniel J. Triplett, Providence, UT (US); Rick Simmons, Carlsbad, CA (US); Larry T. Khoo, Los Angeles, CA (US); Burak M. Ozgur, Los Angeles, CA (US); Bryan Howard, Smithfield, UT (US)

(73) Assignee: OsteoMed, LLC, Addison, TX (US)

( * ) Notice: Subject to any disclaimer, the term of this patent is extended or adjusted under 35 U.S.C. 154(b) by 223 days.

(21) Appl. No.: 13/088,190

(22) Filed: Apr. 15, 2011

(65) Prior Publication Data

US 2012/0022651 A1   Jan. 26, 2012

Related U.S. Application Data

(60) Provisional application No. 61/324,384, filed on Apr. 15, 2010.

(51) Int. Cl.
*A61F 2/44* (2006.01)
*A61F 2/46* (2006.01)
*A61B 17/00* (2006.01)
*A61F 2/00* (2006.01)
*A61B 17/58* (2006.01)
*A61B 17/60* (2006.01)

(52) U.S. Cl.
USPC .......... 623/17.11; 606/86 R; 606/80; 606/104

(58) Field of Classification Search
CPC ................................................... A61B 17/1671
USPC ........................ 606/80, 86 R, 104; 623/17.11
See application file for complete search history.

(56) References Cited

U.S. PATENT DOCUMENTS 447,761 A   3/1891   Clough
832,201 A   10/1906  Fistler (Continued)

FOREIGN PATENT DOCUMENTS

WO   WO 9609013   3/1996
WO   WO 9916499   4/1999

OTHER PUBLICATIONS

Biomet Spine; AccuVision Minimally Invasive Spinal Exposure System, Surgical Technique Dec. 2009.

(Continued)

*Primary Examiner* — David Bates
(74) *Attorney, Agent, or Firm* — Peter K. Johnson

(57) ABSTRACT

Apparatus, systems, and methods for spine surgery employ a guide wire temporarily anchored to a contralateral side of an intervertebral disc. The guide wire establishes a reliable pathway for passage and actuation of cannulated instruments or implants through a small working channel leading to an ipsilateral side of the disc. The guide wire may be disconnected and removed from the disc after use.

15 Claims, 20 Drawing Sheets

(56) References Cited

U.S. PATENT DOCUMENTS

| | | |
|---|---|---|
| 1,839,726 A | 1/1932 | Arnold |
| 1,863,057 A | 6/1932 | Innes |
| 1,944,009 A | 1/1934 | Homer |
| 2,313,164 A | 3/1943 | Nelson |
| 2,586,488 A | 2/1952 | Smith |
| 2,812,758 A | 11/1957 | Blumenschein |
| 2,854,983 A | 10/1958 | Baskin |
| 3,070,088 A | 12/1962 | George |
| 3,087,486 A | 4/1963 | Kilpatrick |
| 3,397,699 A | 8/1968 | Kohl |
| 3,417,746 A | 12/1968 | Moore |
| 3,509,883 A | 5/1970 | Dibelius |
| 3,770,342 A | 11/1973 | Dudragne |
| 3,788,318 A | 1/1974 | Kim |
| 3,789,852 A | 2/1974 | Kim |
| 3,944,341 A | 3/1976 | Pomerantzeff |
| 3,998,217 A | 12/1976 | Trumbull |
| 4,010,741 A | 3/1977 | Gauthier |
| 4,130,113 A | 12/1978 | Graham |
| 4,141,364 A | 2/1979 | Schultze |
| 4,254,763 A | 3/1981 | McCready |
| 4,312,353 A | 1/1982 | Shahbabian |
| 4,545,374 A | 10/1985 | Jacobson |
| 4,589,868 A | 5/1986 | Jacobson |
| 4,716,901 A | 1/1988 | Jackson |
| 4,739,762 A | 4/1988 | Palmaz |
| 4,779,611 A | 10/1988 | Grooters |
| 4,817,587 A | 4/1989 | Janese |
| 4,896,669 A | 1/1990 | Bhate |
| 5,032,113 A | 7/1991 | Burns |
| 5,116,318 A | 5/1992 | Hillstead |
| 5,139,511 A | 8/1992 | Gill |
| 5,183,464 A | 2/1993 | Dubrul |
| 5,312,417 A | 5/1994 | Wilk |
| 5,320,611 A | 6/1994 | Bonutti |
| 5,377,667 A | 1/1995 | Patton |
| 5,383,889 A | 1/1995 | Warner |
| 5,391,156 A | 2/1995 | Hildwein |
| 5,391,178 A | 2/1995 | Yapor |
| 5,425,730 A | 6/1995 | Luloh |
| 5,431,676 A | 7/1995 | Dubrul |
| 5,452,732 A | 9/1995 | Bircoll |
| 5,460,170 A | 10/1995 | Hammerslag |
| 5,496,345 A | 3/1996 | Kieturakis |
| 5,505,690 A | 4/1996 | Patton |
| 5,514,153 A | 5/1996 | Bonutti |
| 5,522,790 A | 6/1996 | Moll |
| 5,580,344 A | 12/1996 | Hasson |
| 5,607,441 A | 3/1997 | Sierocuk |
| 5,653,726 A | 8/1997 | Kieturakis |
| 5,678,572 A | 10/1997 | Shaw |
| 5,688,223 A | 11/1997 | Rosendahl |
| 5,702,417 A | 12/1997 | Hermann |
| 5,728,046 A | 3/1998 | Mayer |
| 5,772,661 A * | 6/1998 | Michelson ................. 606/86 A |
| 5,772,681 A | 6/1998 | Leoni |
| 5,782,854 A | 7/1998 | Hermann |
| 5,827,318 A | 10/1998 | Bonutti |
| 5,827,319 A | 10/1998 | Carlson |
| 5,830,191 A | 11/1998 | Hildwein |
| 5,860,997 A | 1/1999 | Bonutti |
| 5,865,802 A | 2/1999 | Yoon |
| 5,888,196 A | 3/1999 | Bonutti |
| 5,893,866 A | 4/1999 | Hermann |
| 5,919,128 A | 7/1999 | Fitch |
| 5,944,734 A | 8/1999 | Hermann |
| 5,954,739 A | 9/1999 | Bonutti |
| 5,957,832 A | 9/1999 | Taylor |
| 5,967,970 A | 10/1999 | Cowan |
| 5,993,472 A | 11/1999 | Hermann |
| 6,004,337 A | 12/1999 | Kieturakis |
| 6,004,340 A | 12/1999 | Hermann |
| 6,022,340 A | 2/2000 | Sepetka |
| 6,032,671 A | 3/2000 | Mollenauer |
| 6,036,689 A | 3/2000 | Tu |
| 6,079,761 A | 6/2000 | Sedeck |
| 6,080,174 A | 6/2000 | Dubrul |
| 6,083,154 A | 7/2000 | Liu |
| 6,093,173 A | 7/2000 | Balceta |
| 6,102,928 A | 8/2000 | Bonutti |
| 6,139,493 A | 10/2000 | Koros |
| 6,171,299 B1 | 1/2001 | Bonutti |
| 6,187,023 B1 | 2/2001 | Bonutti |
| 6,206,826 B1 | 3/2001 | Mathews |
| 6,206,886 B1 * | 3/2001 | Bennett .................. 606/104 |
| 6,235,043 B1 | 5/2001 | Reiley |
| 6,267,424 B1 | 7/2001 | Gillette |
| 6,277,136 B1 | 8/2001 | Bonutti |
| 6,312,443 B1 | 11/2001 | Stone |
| 6,322,500 B1 | 11/2001 | Sikora |
| 6,325,812 B1 | 12/2001 | Dubrul |
| 6,387,095 B1 | 5/2002 | Kennett |
| 6,436,119 B1 | 8/2002 | Erb |
| 6,464,634 B1 | 10/2002 | Fraser |
| 6,464,697 B1 | 10/2002 | Edwards |
| 6,468,205 B1 | 10/2002 | Mollenauer |
| 6,494,893 B2 | 12/2002 | Dubrul |
| 6,564,078 B1 | 5/2003 | Marino |
| 6,569,182 B1 | 5/2003 | Balceta |
| 6,592,602 B1 | 7/2003 | Peartree |
| 6,632,234 B2 | 10/2003 | Kieturakis |
| 6,689,152 B2 | 2/2004 | Balceta |
| 6,692,462 B2 | 2/2004 | Mackenzie |
| 6,814,715 B2 | 11/2004 | Bonutti |
| 6,866,676 B2 | 3/2005 | Kieturakis |
| 6,869,398 B2 | 3/2005 | Obenchain |
| 6,921,364 B2 | 7/2005 | Mollenauer |
| 6,948,751 B2 | 9/2005 | Wooten |
| 7,079,883 B2 | 7/2006 | Marino |
| 7,195,592 B2 | 3/2007 | Ravikumar |
| 7,217,273 B2 | 5/2007 | Bonutti |
| 7,235,064 B2 | 6/2007 | Hopper |
| 7,294,136 B2 | 11/2007 | Dubrul |
| 7,311,719 B2 | 12/2007 | Bonutti |
| 7,326,226 B2 | 2/2008 | Root |
| 7,329,268 B2 | 2/2008 | Van Nguyen |
| 7,344,495 B2 | 3/2008 | Ravikumar |
| 7,396,329 B2 | 7/2008 | Nakao |
| 7,435,219 B2 | 10/2008 | Kim |
| 7,476,232 B2 | 1/2009 | Deal |
| 7,488,337 B2 | 2/2009 | Saab |
| 7,510,524 B2 | 3/2009 | Vayser |
| 7,556,600 B2 | 7/2009 | Landry |
| 7,645,232 B2 | 1/2010 | Shluzas |
| 7,682,378 B2 * | 3/2010 | Truckai et al. ................. 606/279 |
| 7,874,982 B2 | 1/2011 | Selover |
| 7,909,832 B2 | 3/2011 | Michelson |
| 7,935,053 B2 | 5/2011 | Karpowicz |
| 7,985,179 B2 | 7/2011 | Gephart |
| 7,988,624 B2 | 8/2011 | Smith |
| 8,105,236 B2 | 1/2012 | Malandain |
| 8,114,161 B2 * | 2/2012 | Evans et al. ................. 623/17.16 |
| 8,137,284 B2 | 3/2012 | Miles |
| 8,172,750 B2 | 5/2012 | Miles |
| 8,182,423 B2 | 5/2012 | Miles |
| 2001/0039430 A1 | 11/2001 | Dubrul |
| 2002/0193822 A1 | 12/2002 | Hung |
| 2003/0018352 A1 | 1/2003 | Mollenauer |
| 2003/0023259 A1 | 1/2003 | Dubrul |
| 2003/0181939 A1 | 9/2003 | Bonutti |
| 2003/0195405 A1 | 10/2003 | Marino |
| 2003/0225432 A1 | 12/2003 | Baptiste |
| 2003/0233115 A1 | 12/2003 | Eversull |
| 2004/0243158 A1 | 12/2004 | Konstantino |
| 2004/0243167 A1 | 12/2004 | Tanaka |
| 2005/0124937 A1 | 6/2005 | Kick |
| 2005/0182436 A1 | 8/2005 | Chopra |
| 2005/0234493 A1 | 10/2005 | Carr |
| 2006/0052750 A1 | 3/2006 | Lenker |
| 2006/0135981 A1 | 6/2006 | Lenker |
| 2006/0135987 A1 | 6/2006 | Jones |
| 2006/0258951 A1 * | 11/2006 | Bleich et al. ................. 600/546 |
| 2007/0032703 A1 | 2/2007 | Sankaran |
| 2007/0049962 A1 | 3/2007 | Marino |

(56) References Cited

U.S. PATENT DOCUMENTS

| | | | |
|---|---|---|---|
| 2007/0168043 A1* | 7/2007 | Ferree | 623/17.16 |
| 2008/0064945 A1 | 3/2008 | Marino | |
| 2008/0065135 A1 | 3/2008 | Marino | |
| 2008/0065140 A1 | 3/2008 | Bonutti | |
| 2008/0065144 A1 | 3/2008 | Marino | |
| 2008/0103519 A1 | 5/2008 | Bonutti | |
| 2008/0109026 A1 | 5/2008 | Kassam | |
| 2008/0132764 A1 | 6/2008 | Hamada | |
| 2008/0147109 A1 | 6/2008 | Kambin | |
| 2008/0221586 A1 | 9/2008 | Garcia-Bengochea | |
| 2008/0255563 A1 | 10/2008 | Farr | |
| 2009/0036744 A1 | 2/2009 | Vayser | |
| 2009/0062871 A1 | 3/2009 | Chin | |
| 2010/0041955 A1 | 2/2010 | Grey | |
| 2010/0160947 A1 | 6/2010 | Akyuz | |
| 2012/0010472 A1 | 1/2012 | Spann | |
| 2012/0101341 A1 | 4/2012 | Malandain | |

OTHER PUBLICATIONS

Aesculap Spine; Caspar Cervical Retractor System, Product Brochure Apr. 2009.
Zimmer; ARAS Retractor, Surgical Technique L1377 Rev. A 2007.
Depuy; Pipeline Concorde, Surgical Technique Jul. 2007 M102-20-001.
Zimmer Spine; Harmony Retractor System, Surgical Technique L1477 Rev. A Aug. 2009.
LANX; Timberline Lateral Fusion System, Surgical Technique LIT8710-0111.03.
Medtronic; Mast Quadrant, Product Brochure 2005 MLITQUDST5.
Synthes; Oracle Spacer, Technique Guide Dec. 2010 J8158-C.
K2M; Tera Nova, Product Brochure 2012 K2-15-7002-01 Rev. 3.
Biomet Spine; VuePASS, Surgical Technique Jun. 2007 P/N 216001L.
NuVasive; Maxcess-XLIF, Surgical Technique 2007 9500138 A.0.

* cited by examiner

DIRECT LATERAL SPINE SYSTEM INSTRUMENTS, IMPLANTS AND ASSOCIATED METHODS

CROSS-REFERENCE TO RELATED APPLICATIONS

This application claims the benefit of the filing date of:

U.S. Application No. 61/324,384 filed Apr. 15, 2010, entitled DIRECT LATERAL SPINE SYSTEM—INSTRUMENTS, IMPLANTS AND ASSOCIATED METHODS, which is pending.

The above-identified document is incorporated herein by reference.

BACKGROUND OF THE INVENTION

The present disclosure relates to orthopedics, and more particularly, to apparatus, systems, and methods for spinal surgery through a lateral approach.

The lateral approach to the spine is appealing because it avoids the major neural and vascular structures on the anterior and posterior aspects of the spine. However, the lateral approach may encounter other sensitive structures, such as the psoas muscle, neural plexus, vascular plexus, or other peritoneal structures. The psoas muscle is of particular interest because it is highly innervated. Therefore, insult to the psoas muscle is quite painful. Surgical procedures or approaches which minimize trauma to the psoas muscle may reduce postoperative pain and improve outcomes.

BRIEF DESCRIPTION OF THE DRAWINGS

Various embodiments will now be discussed with reference to the appended drawings. It is appreciated that these drawings depict only typical embodiments and are therefore not to be considered limiting of the scope of the invention as set forth in the claims.

DETAILED DESCRIPTION OF THE PREFERRED EMBODIMENTS

The present disclosure relates to systems and methods for direct lateral approach spine surgery. Those of skill in the art will recognize that the following description is merely illustrative of principles which may be applied in various ways to provide many different alternative embodiments. This description is made for the purpose of illustrating the general principles and is not meant to limit the inventive concepts in the appended claims.

One principle in the present disclosure is to reduce trauma to the psoas muscle. For example, the present disclosure teaches that the discectomy portion of a spinal procedure may be performed through a very small working portal. In another example, the present disclosure teaches that all instruments may be cannulated or otherwise adapted to be guided into the disc space by a guide-wire that is anchored to the disc annulus and/or vertebral body. These guided instruments would not require visualization of the procedural site, allowing for the minimal dissection size. In yet another example, at least some of the instruments may expand at the distal (working) tip to clear a path larger than that created outside the disc space by the access corridor. Once the discectomy is complete, the corridor through the psoas may be dilated to a larger size to accommodate implant placement.

A segmented fusion cage is disclosed. With a segmented implant, the entire procedure may be performed through a smaller working cannula. It may not be necessary to dilate the access corridor to a larger size after discectomy for fusion cage placement. The disclosed segmental fusion cage may be in two parts, so that half of the implant may be placed, followed by the other half.

Various apparatus, systems and methods will now be described with reference to the drawings.

Figure 1:
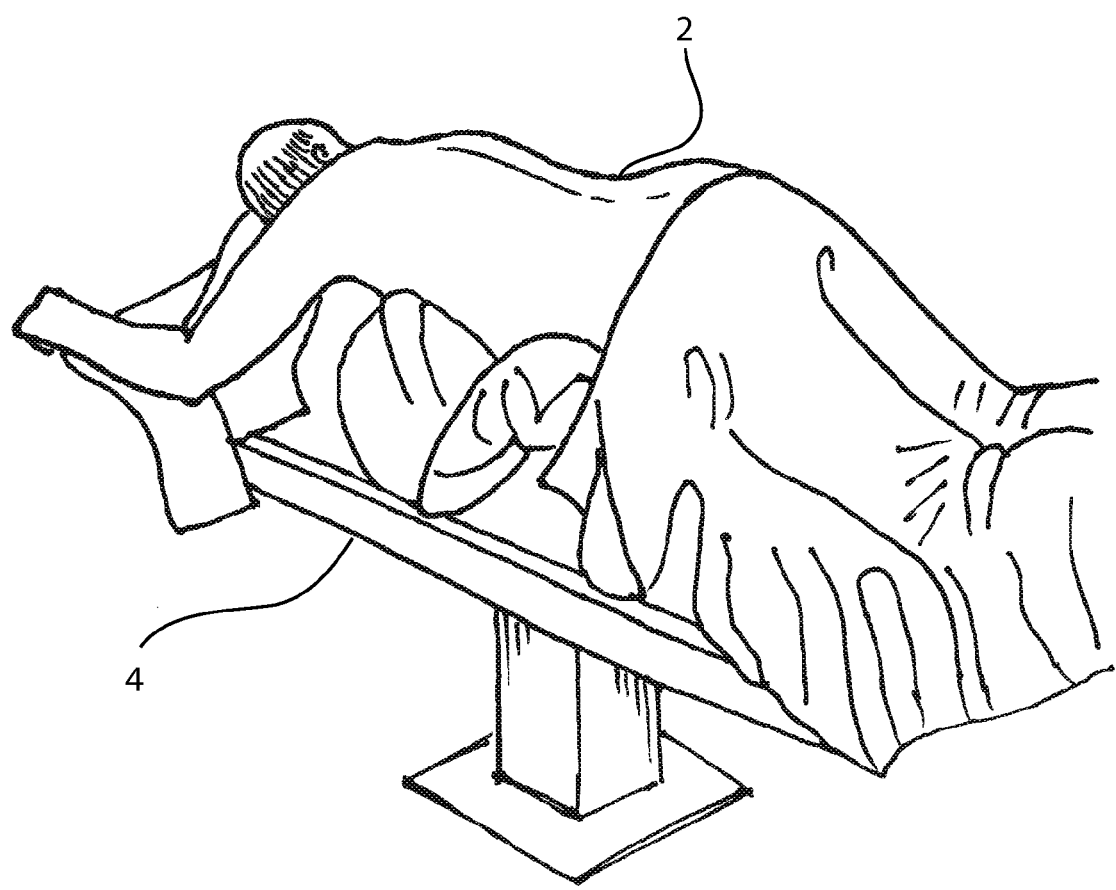
FIG. 1 is a perspective view of a patient in a prone position on a surgical table.

A method of positioning a patient 2 for lateral spine surgery may place the patient 2 in a prone position, as illustrated in FIG. 1. A radiolucent surgical table 4 may be used in order to position the patient 2 optimally and provide an unrestricted view for imaging. The table 4 may allow the abdominal contents to hang freely for safer navigation through the retroperitoneal space, and to ease venous drainage. Arms and legs may be supported as necessary. Bony prominences may be padded. The patient 2 may be secured to the table 4 and immobilized to minimize shifting during the procedure.

Figure 2:
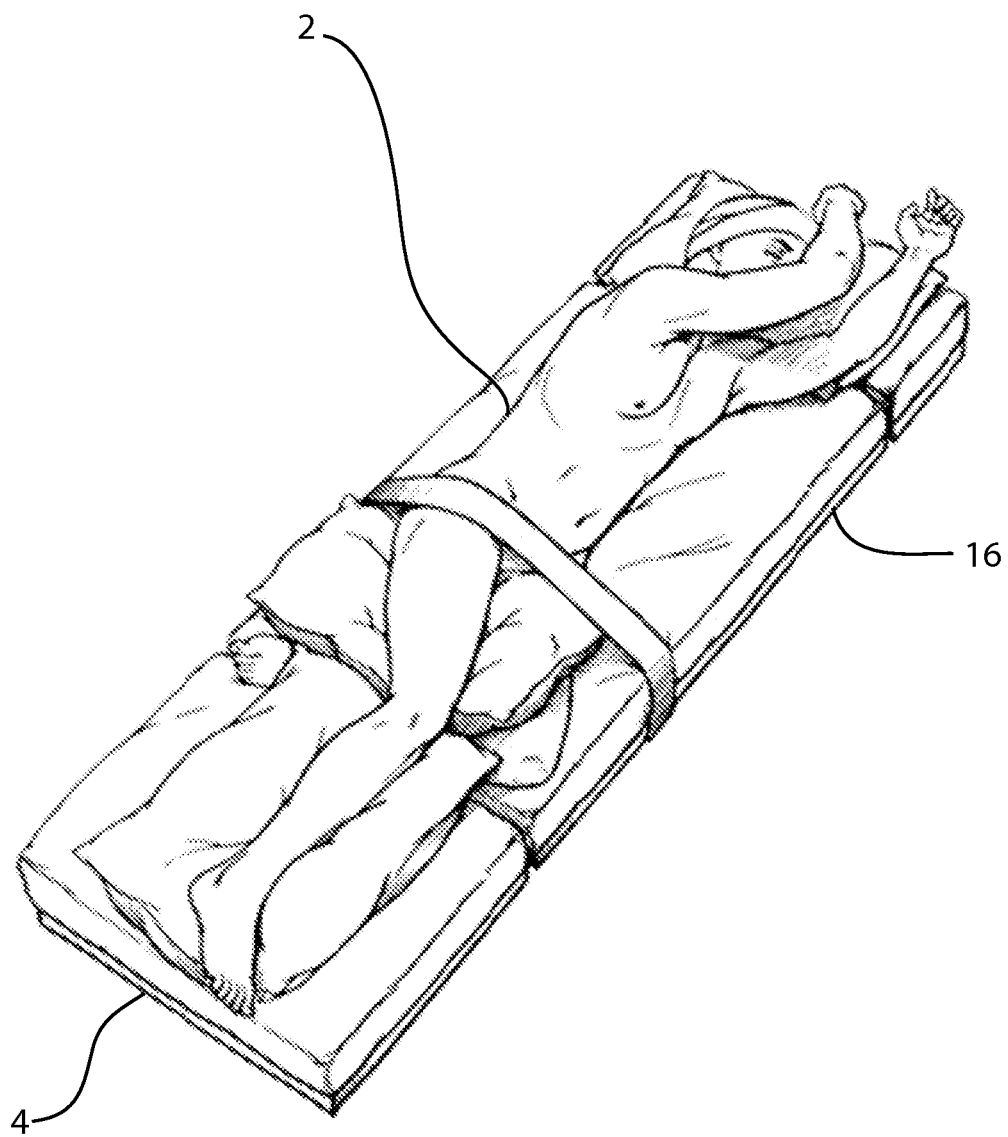
FIG. 2 is a perspective view of a patient in a lateral decubitus position on a surgical table.

Another method of positioning a patient 2 for lateral spine surgery may place the patient 2 in a lateral decubitus position, as illustrated in FIG. 2. A bendable surgical table 4 may be used in order to position the patient 2 optimally. It may be helpful to position the patient 2 so that the iliac crest is directly over a bend, or break, in the table 4. This may allow the pelvis to tilt away from the spine, and may provide clear access to the lumbar spine, such as the L4-L5 level. The patient 2 may be supported, padded, secured, and immobilized similar to the above description for the prone position.

Regardless of the patient position, the table 4 may provide one or more rails 16 to which apparatus may be secured. Specialized adapters may be useful with certain tables, depending on rail design.

After the patient 2 is prepared and draped, fluoroscopy may be used to locate the relevant spinal anatomy. The use of biplanar fluoroscopy may facilitate this step. Anatomy may be marked on the skin for later reference.

Figure 3:
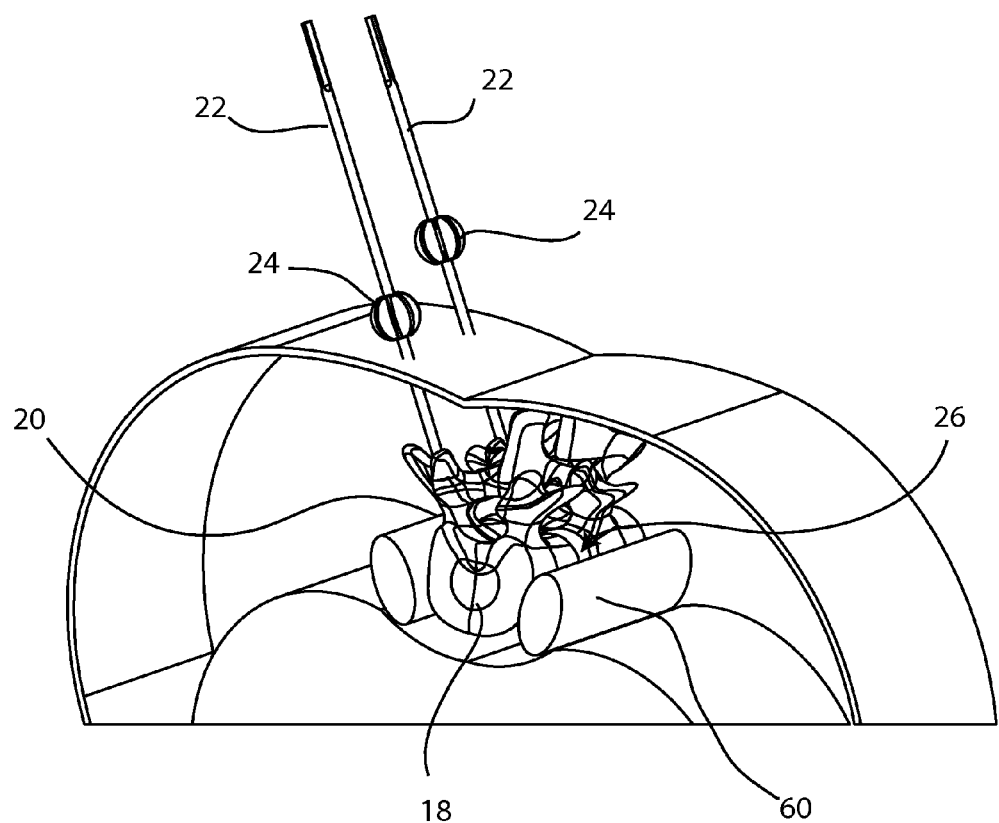
FIG. 3 is a perspective view of Caspar pins and spheres in pedicles on the same side of adjacent vertebrae in a segment of a torso.

FIG. 3 illustrates an optional step which may be used when the patient 2 is in the prone position. The table 4 and C-arm (not shown) may be oriented to provide distinct anterior-posterior and lateral images of the vertebral endplates 18. A Jamshidi needle (not shown) may be used to target the contralateral pedicle 20, and its location verified with biplanar fluoroscopy. A k-wire (not shown) may be placed through the Jamshidi outer sheath, which may then be removed. A Caspar pin 22 may be screwed into the pedicle 20 over the k-wire, and a split clamping sphere 24 attached to the Caspar pin 22. This optional step may be repeated at each operative level.

Figure 4:
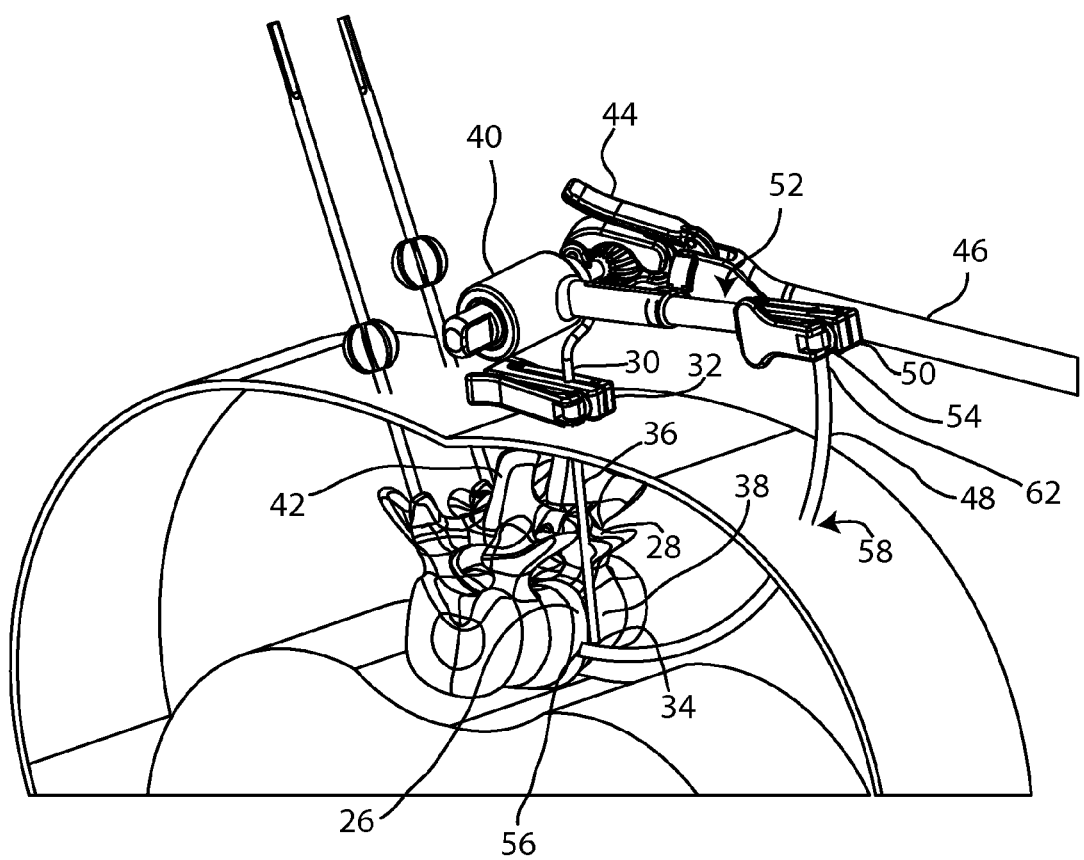
FIG. 4 is a perspective view of the pins and spheres of FIG. 3 with a targeting apparatus oriented and positioned relative to an intervertebral disc between the vertebrae.

A method of locating the appropriate disc space may rely upon a targeting post 30. This method is illustrated in FIG. 4 for a curved lateral approach. The appropriate disc space 26 may be located prior to making the skin incision. The location of the superior edge of the transverse process-pedicle junction 28 in the anterior-posterior plane may be determined and a tiny stab hole made with a scalpel blade. A targeting post 30 with a depth stop 32 may be inserted onto the transverse process-pedicle junction 28. The targeting post 30 may then slide over the superior edge of the transverse process-pedicle junction 28. A nerve monitoring cable alligator clip (not shown) may be attached as well.

The targeting post 30 may be positioned and oriented so that the tip 34 of the obturator 36 is seated at the midpoint of the superior endplate 18 of the inferior vertebra 38. Lateral fluoroscopy may be used to verify the position of the obturator tip 34. The targeting post depth stop mechanism 32 may be engaged. The obturator 36 may be oriented collinear with the superior endplate 18 of the inferior vertebra 38. Lateral fluoroscopy may be used to verify the orientation of the obturator 36. The micrometer 40 may be aligned with the spinous processes 42 and its position verified by anterior-posterior fluoroscopy. The targeting post 30 may be affixed to the clamp on the articulating surgical support arm.

The initial dilator 48 may be inserted into the offset arm 50 of the targeting apparatus 52 using the cam clamp 54. The initial dilator 48 shown in FIG. 4 is curved, although a straight dilator may be used instead. The initial dilator 48 may be attached to the targeting post 30. The telescoping offset arm 50 may be fully extended. The distal tip 56 of the initial dilator 48 may be swung onto the body. A skin marker may be used to mark the initial incision location 58.

An incision may be made through the skin into the initial fascial plane. The skin incision may be extended through the muscle fibers of the external and internal obliques and transversus abdominis. The initial incision may be large enough to permit finger dissection. Once through the abdominal muscles, blunt finger dissection may be used to access the retroperitoneal space. These anatomical structures are not shown but are well documented elsewhere, for example, in anatomy texts. Blunt finger dissection may extend down the transverse process to the psoas muscle 60. Optionally, a slender blunt instrument, such as a Kittner probe (not shown), may be used to gently dissect through the psoas muscle 60 between the middle and anterior third. One or more peritoneal retractors (not shown) may be used, as necessary. A neural monitoring system (not shown) may be clipped to the retractors.

An electrode (not shown) may be attached to the proximal end 62 of the initial dilator 48. Some or all of the dilators disclosed herein may include insulation to decrease current shunting whenever there is an exposed distal electrode at the tip of the dilator that acts as the stimulation source. The initial dilator 48 may be inserted all the way through the psoas muscle 60 up to the disc space 26, while observing the neural monitoring system, as shown in FIG. 4. The descending nerves of the lumbar plexus lie in the posterior third of the psoas muscle 60. Intra-operative neural monitoring may facilitate safe passage past these nerves and may confirm their location with evoked electromyogram (EMG) monitoring. As the dilators advance through the psoas muscle 60, the stimulus necessary to elicit an EMG response may vary based on the proximity of the dilator to the lumbar plexus. The closer the stimulus source is to the nerve, the less intensity may be required to elicit a response. The literature suggests that threshold values greater than 10 mA may correlate to a distance that allows for both continued nerve safety and ample working space. Values less than 10 mA may be regarded as being too close to the exiting nerve root. In this situation, it may be advisable to reposition the dilator. Cranial-caudal adjustments may be made with the micrometer 40 so that the distal tip 56 of the initial dilator 48 is in a mid-disc location of the affected disc 26. Lateral fluroroscopy may be used to verify the position of the initial dilator tip 56. The anterior-posterior dilator location and nerve location may be confirmed with neural monitoring prior to placing the guide pin.

A guide pin or k-wire (not shown) may be placed down the first dilator 48 and may be inserted into the disc space 26 to secure the dilator 48. The guide pin or k-wire may be inserted at least half way across the disc space 26. The position of the guide pin or k-wire may be verified with biplanar fluoroscopy.

Another method of locating the appropriate disc space may use the services of an interventional radiologist. This method is not illustrated in the present disclosure. Prior to the surgical procedure, the interventional radiologist may place catheters within each operative disc space 26. Catheters may be placed under conscious sedation. For example, an introducer needle may be placed on or in the outer annulus, with the optional use of biplanar fluoroscopy. A guide wire may be introduced through the needle and into the disc space 26. A catheter may be placed over the guide wire and through the introducer needle into the nucleus, after which the guide wire and needle may be removed. The balloon anchor of the catheter may be slightly inflated to anchor the catheter within the disc space. For example, the balloon may be inflated with contrast medium. The proximal end of the catheter may be capped and secured to the patient 2 with sterile tape. The patient 2 may then be transferred to the operating room for lateral access spine surgery.

When the lateral access spine surgery begins, a new guide wire may be introduced through the catheter directly into the disc space 26. The catheter may then be removed. The guide wire may be used to establish a safe operative corridor to the lateral spine.

Figure 5A:
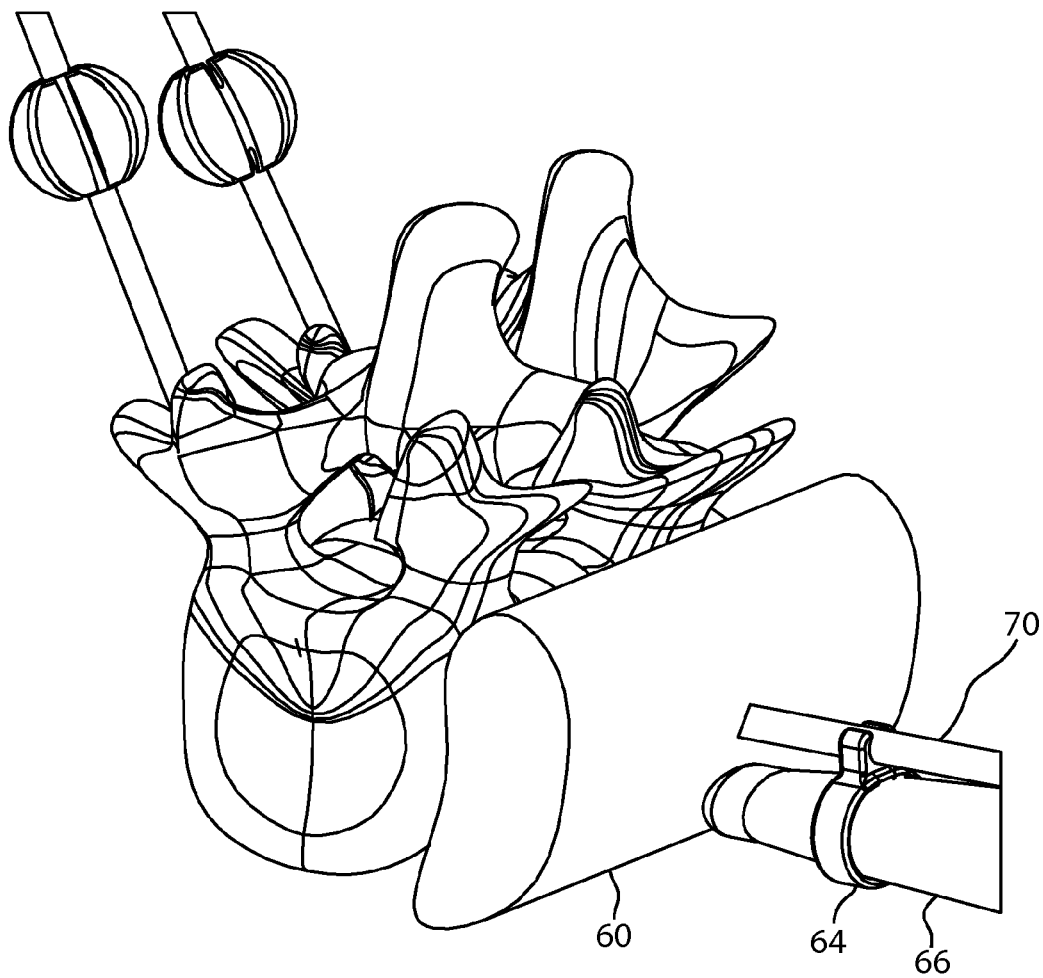
FIG. 5A is a perspective view of the pins and spheres of FIG. 3 with a stylus oriented and positioned relative to the intervertebral disc.
Figure 5B:
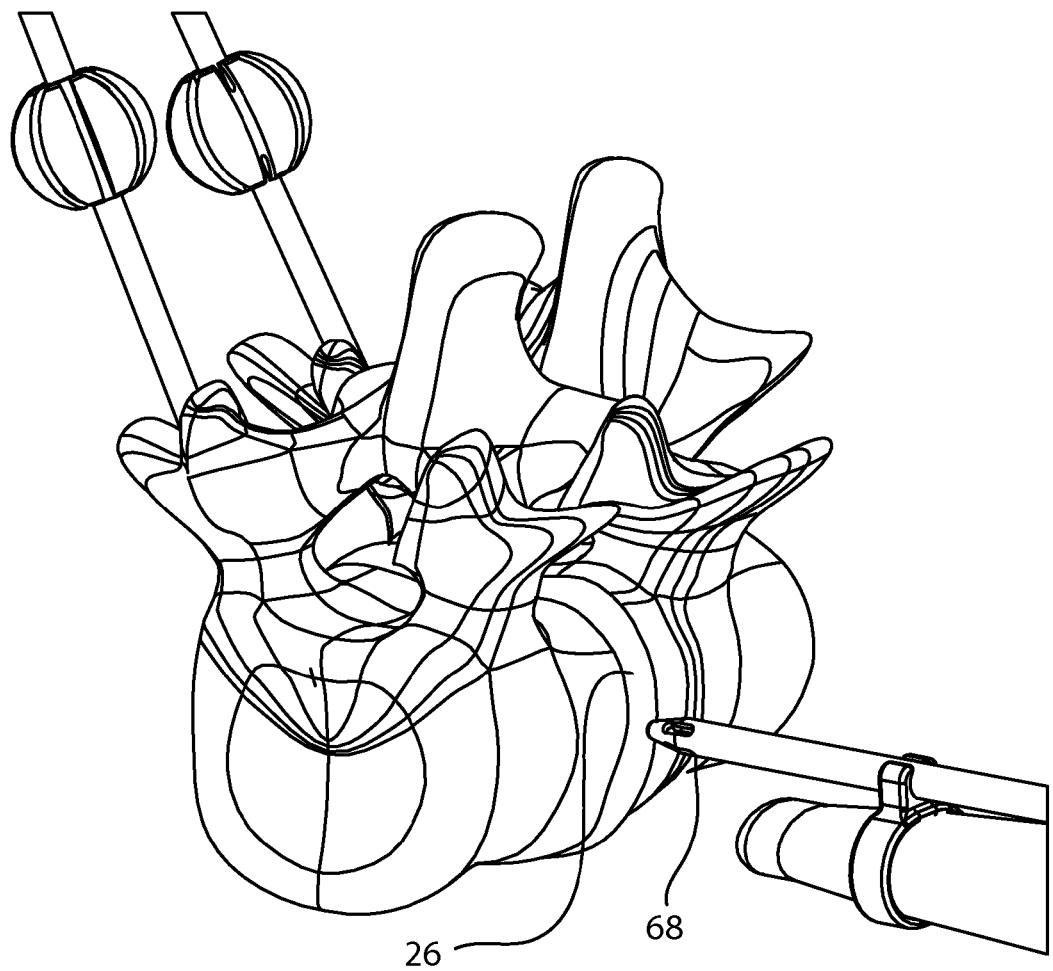
FIG. 5B is the perspective view of FIG. 5A with the psoas muscle omitted for clarity.
Figure 6:
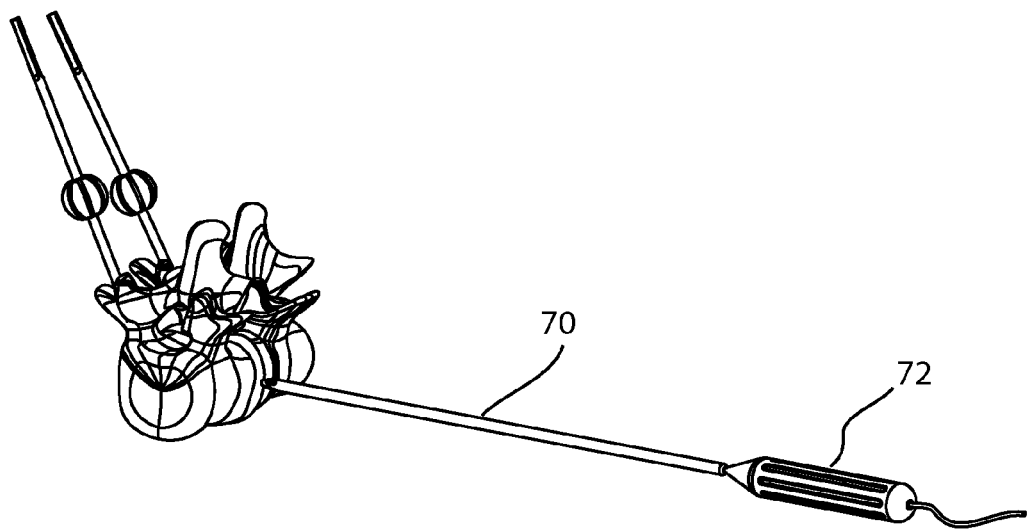
FIG. 6 is a perspective view of the pins, spheres, and stylus of FIGS. 5A-5B with a neural monitoring probe inserted inside the stylus.
Figure 7:
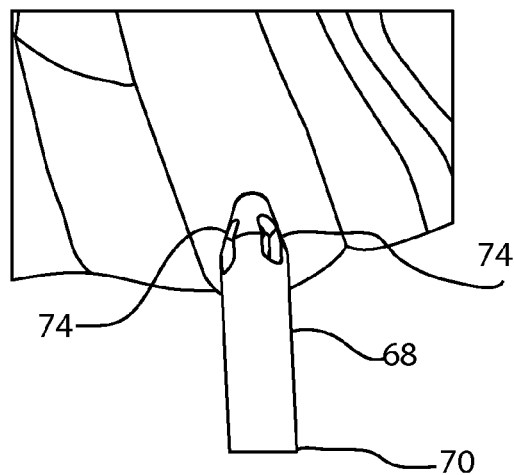
FIG. 7 is an enlarged detail view of the tip of the stylus and a portion of the intervertebral disc.

Yet another method of locating the appropriate disc space may rely upon manual finger palpation. This method is illustrated in FIGS. 5A-7 for a straight, or direct, lateral approach. A lateral skin incision may be made through the skin into the initial fascial plane. The initial incision may be large enough to permit blunt finger dissection. Once through the abdominal muscles, blunt finger dissection may be used to access the retroperitoneal space, the transverse process, and the psoas muscle 60. A stylus guide ring 64 may be placed over the middle phalange of the index finger 66. The stylus tip 68 may be inserted onto the guide ring 64, and the index finger 66 may be re-inserted to the psoas muscle 60 at the desired level. The stylus 70 may be introduced through the psoas muscle 60 and into the disc space 26, as illustrated in FIG. 5A, and in FIG. 5B with the psoas muscle 60 removed for clarity. The stylus illustrated in FIGS. 5A-5B is straight, although a curved stylus may be used instead. A cranial-caudal sweeping motion may be effective in separating the psoas muscle fibers during the dilation phase. The stylus 70 may slidably receive the neural monitoring probe 72 inside, as shown in FIG. 6. The probe 72 may transmit signals through apertures 74 at the tip 68 of the stylus 70, as shown in FIG. 7. Once proper seating of the stylus 70 has been confirmed, the location may be maintained by inserting a k-wire through the central lumen of the stylus 70 and into the disc space 26.

Figure 8:
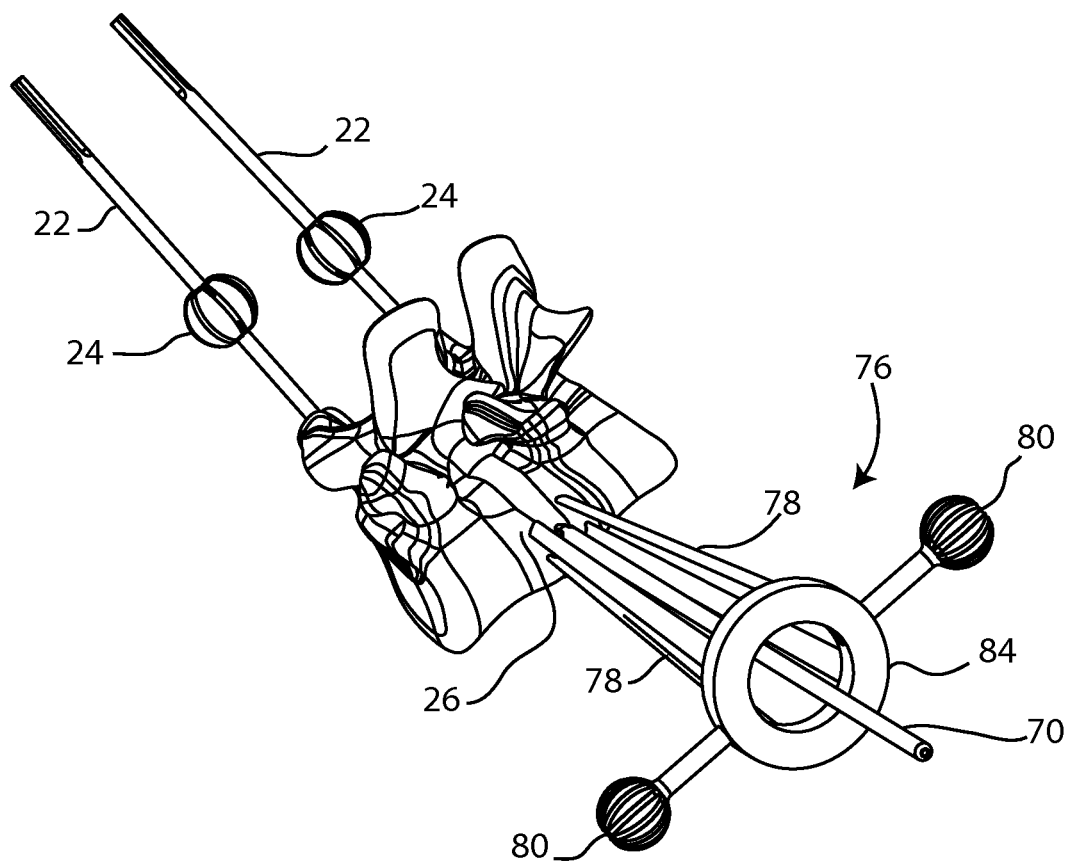
FIG. 8 is a perspective view of the pins, spheres, and stylus of FIGS. 5A-5B with a retractor positioned over the stylus.
Figure 9:
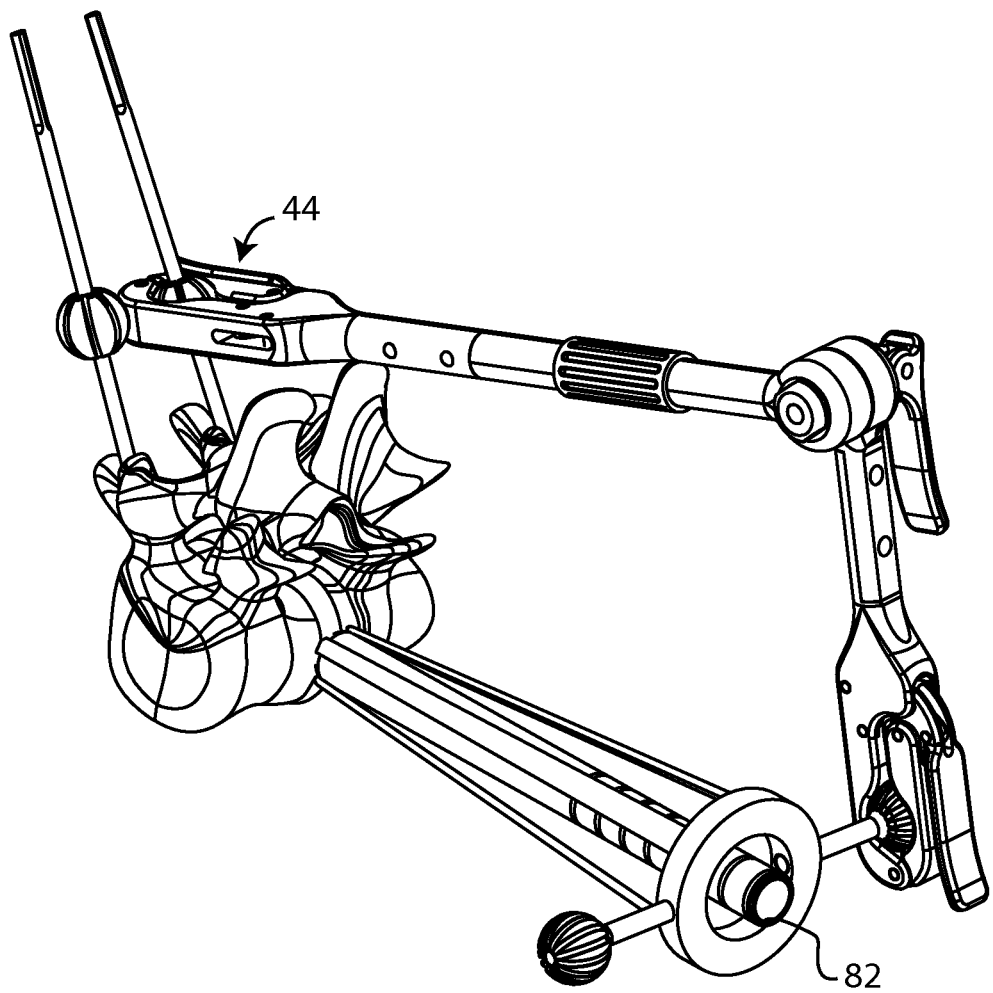
FIG. 9 is a perspective view of the pins, spheres, and retractor of FIG. 8 with the retractor docked to a sphere on a pin, and with a dilator positioned within the retractor.
Figure 10:
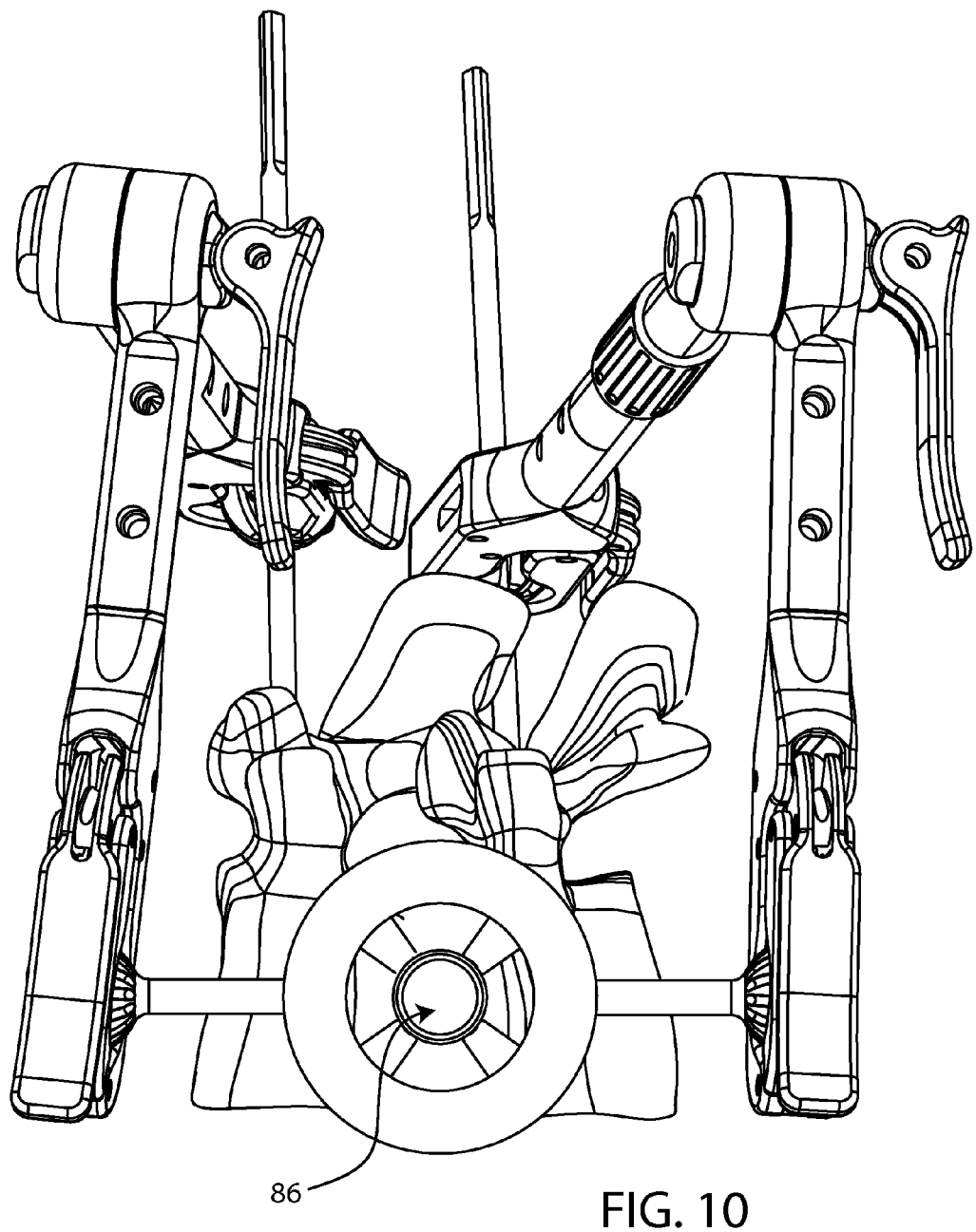
FIG. 10 is a lateral view of the pins, spheres, retractor, and dilator of FIG. 9, showing the retractor docked to both pins.

A method of placing a retractor 76 and dilating surrounding tissues may dock the retractor 76 to the spine. This method is illustrated in FIGS. 8-10 for a straight, or direct, lateral approach. The proper length of the dilator blades 78 may be determined from depth markings on the stylus 70. The retractor blades 78 may be introduced slowly over the initially placed stylus 70 until the lateral aspect of the vertebral body is reached, as shown in FIG. 8. The retractor housing spheres 80 may be locked to the spheres 24 on the Caspar pins 22 using the articulating polyaxial clamps 44. The location of the retractor blades 78 may be verified in both the anterior-posterior and the lateral views with fluoroscopy. The retractor 76 may be dilated to the desired diameter for discectomy using sequential tubular dilators 82 up to the desired size, as shown in FIGS. 9-10. The retractor blades 78 may dilate more near the retractor housing 84 and less near the disc space 26. Alternately, the retractor blades 78 may remain parallel, or they may angle outwardly near the disc space 26. A k-wire or shim (not shown) may be placed into the disc space 26 or vertebral body through the lumen 86 of the working dilator 82.

Figure 11:
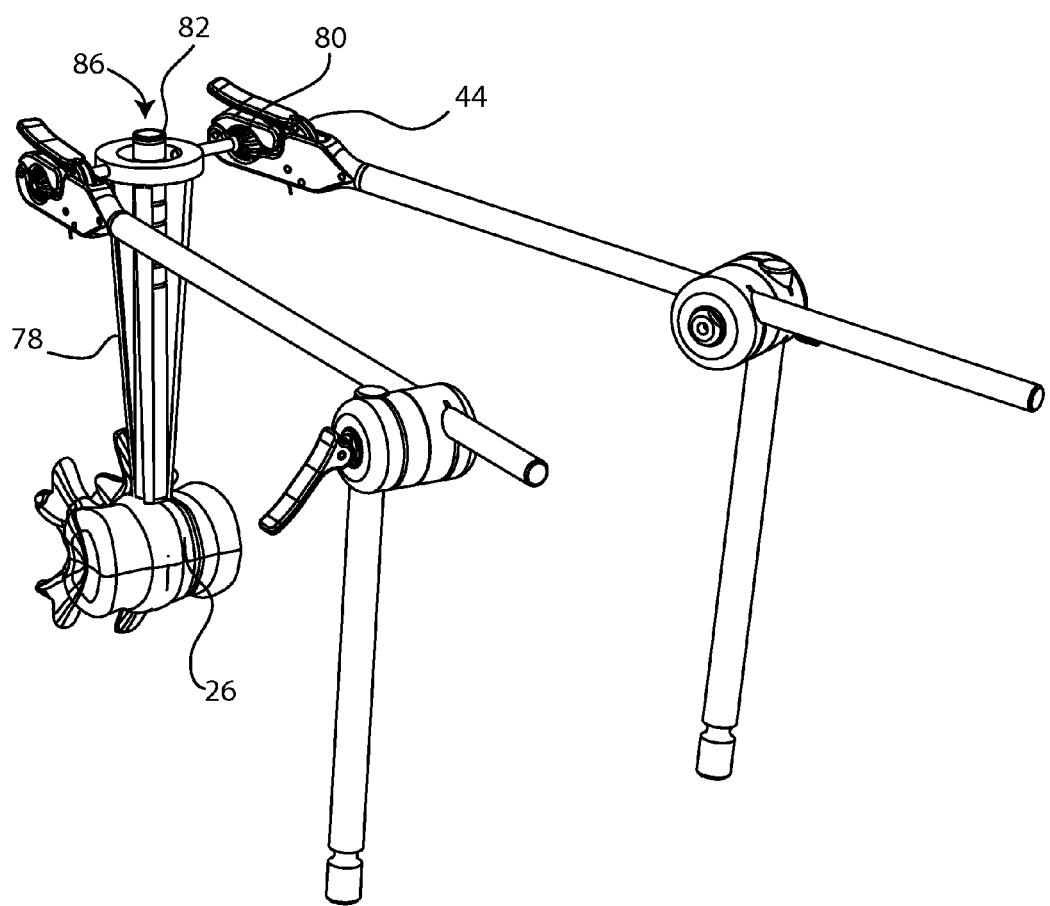
FIG. 11 is a perspective view of the pins, spheres, and retractor of FIG. 8 with the retractor docked to a rail of a surgical table, and with a dilator positioned within the retractor.

Another method of placing a retractor and dilating surrounding tissues may dock at least a portion of the apparatus to a rail 16 of the table 4. This method is illustrated in FIG. 11 for a direct lateral approach. The proper length of the dilator blades 78 may be determined from depth markings on the stylus 70. The retractor blades 78 may be introduced slowly over the initially placed stylus 70 until the lateral aspect of the vertebral body is reached. The retractor housing spheres 80 may be locked to the surgical table rail 16 using the articulating polyaxial clamps 44, as shown in FIG. 11. The location of the retractor blades 78 may be verified in both the anterior-posterior and the lateral views with fluoroscopy. The retractor 76 may be dilated to the desired diameter for discectomy using sequential tubular dilators 82 up to the desired size. The retractor blades 78 may dilate more near the retractor housing 84 and less near the disc space 26. Alternately, the retractor blades 78 may remain parallel, or they may angle outwardly near the disc space 26. A k-wire or shim (not shown) may be placed into the disc space 26 or vertebral body through the lumen 86 of the working dilator 82.

Figure 12:
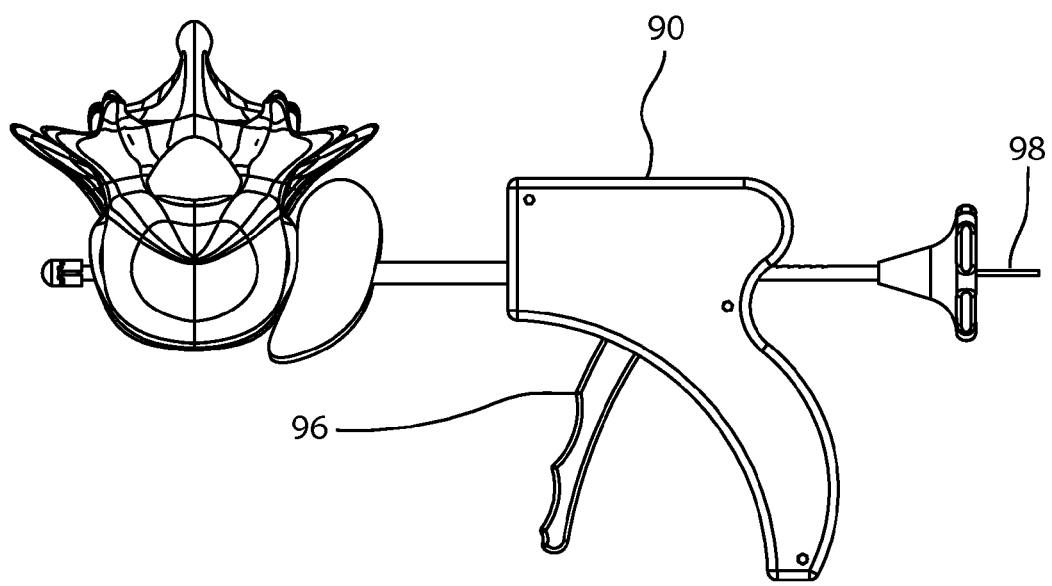
FIG. 12 is a cephalad view of an anchor and inserter instrument positioned and oriented relative to the vertebrae, with the anchor in an insertion configuration.
Figure 13:
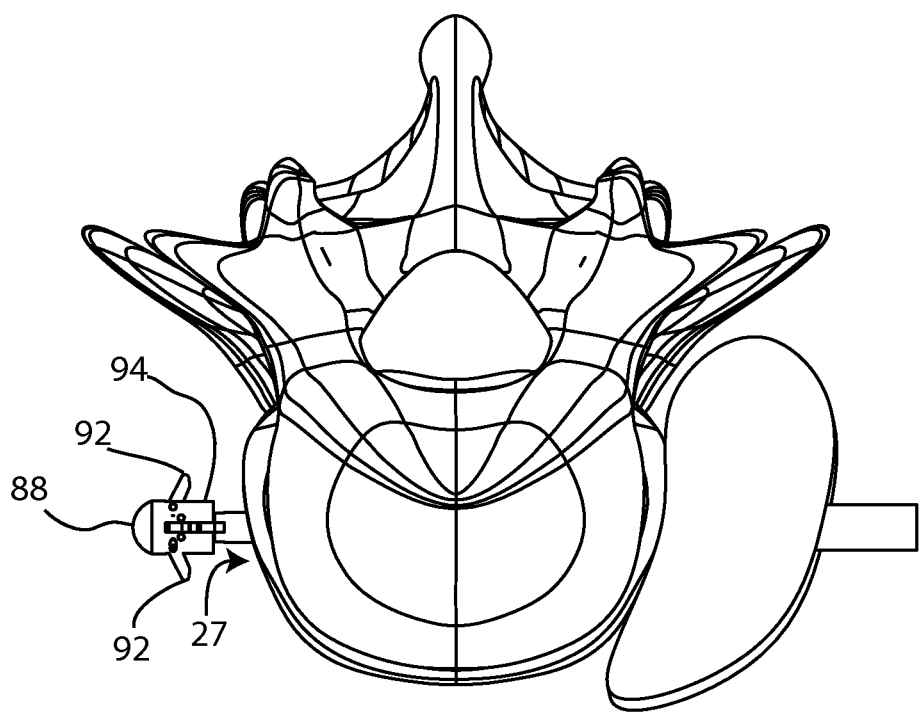
FIG. 13 is an enlarged cephalad view of the anchor of FIG. 12 in a deployed configuration.
Figure 14:
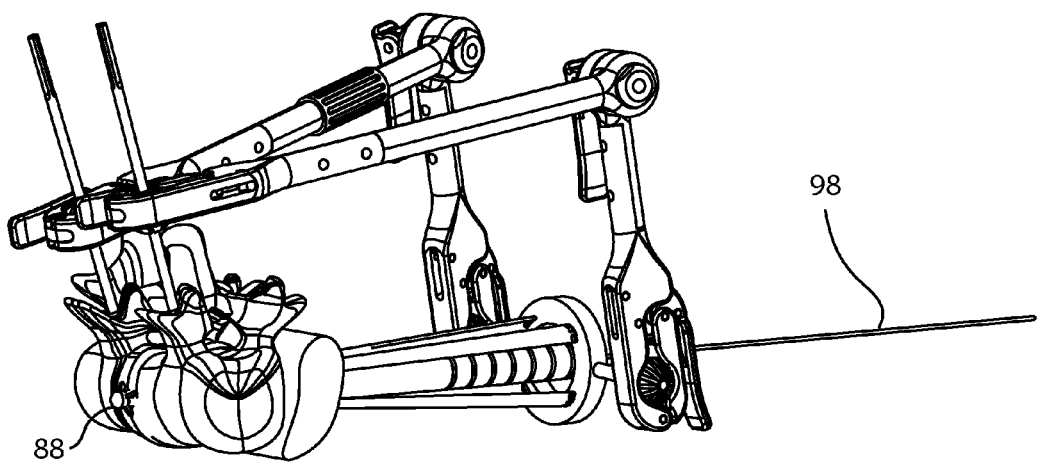
FIG. 14 is a perspective view of the pins, spheres, retractor, and dilator of FIG. 9 with the anchor of FIG. 13 positioned on the contralateral side of the disc from the retractor.

A method for placing an anchor 88 on a contralateral side 27 of the disc 26 may deploy an anchor 88 that resembles a grappling hook. This method is shown in FIGS. 12-14. A trephine or other coring tool (not shown) may be used to establish a pathway or hole through the annulus. An anchor 88 may be secured to an anchor inserter instrument 90. The anchor 88 may also be coupled to a portion of a guide wire 98. For example, the anchor 88 may be coupled to one end of the guide wire 98. When the anchor 88 is secured to the anchor inserter instrument 90, the guide wire 98 may rest in a central cannulation in the instrument 90. The anchor 88 may resemble a grappling hook. The anchor 88 may have one or more movable hooks 92 or tabs which may move between an insertion position, in which the hooks 92 are close to a body 94 of the anchor 88, and a deployed position, in which the hooks 92 project laterally from the body 94 of the anchor 88. In the insertion position, the anchor 88 may be described as having a smaller projected area normal to a center longitudinal axis of the guide wire 98. In the deployed position, the anchor 88 may be described as having a larger projected area. The anchor inserter instrument 90 may be aligned with the pathway or hole previously established by the coring tool. As shown in FIG. 12, the anchor 88 may be inserted into the hole and pushed across the disc space 26 by squeezing the handle 96 of the inserter instrument 90. When the anchor 88 is through the contralateral annulus, the hooks 92 may be moved from the insertion position to the deployed position, as shown in FIG. 13. For example, the hooks 92 may be deployed by pulling on the guide wire 98 to rotate the hooks 92 outwardly from the body 94. The anchor 88 may be seated against or partially within the contralateral annulus by pulling back on the inserter 90. The anchor 88 may disassociate from the inserter instrument 90 when the pulling force exceeds a predetermined threshold value. The inserter instrument 90 may then be removed, leaving the anchor 88 and the guide wire 98 in place, as shown in FIG. 14. In this way, the anchor may be described as connecting the guide wire 98 to the disc 26. The anchor may be removed when desired by sliding the inserter instrument 90 over the guide wire 98 to the anchor body 94, reconnecting the instrument 90 to the body 94, pushing on the instrument 90 to separate the anchor 88 slightly from the contralateral annulus, pushing on the guide wire 98 to move the hooks 92 from the deployed position to the insertion position, and pulling the anchor 88 back out of the disc space 26.

Figure 15:
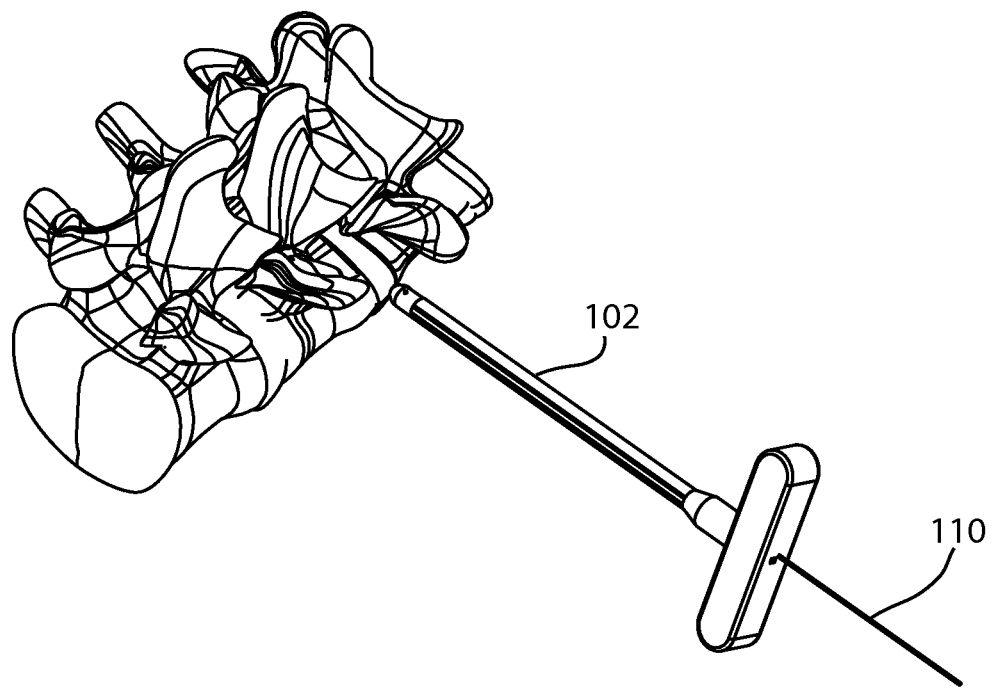
FIG. 15 is a perspective view of another anchor and inserter instrument positioned and oriented relative to the vertebrae, with the anchor in an insertion configuration on an ipsilateral side of the disc to the inserter.
Figure 16:
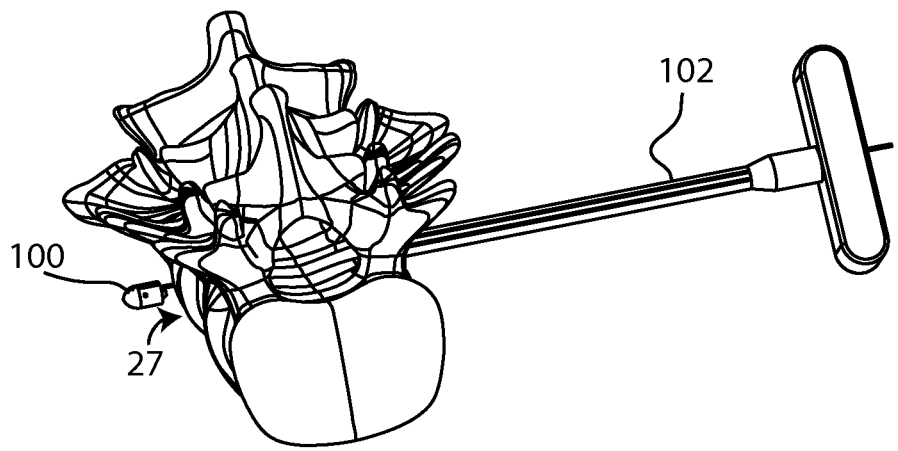
FIG. 16 is a perspective view of the anchor of FIG. 15 positioned on the contralateral side of the disc from the inserter instrument.
Figure 17:
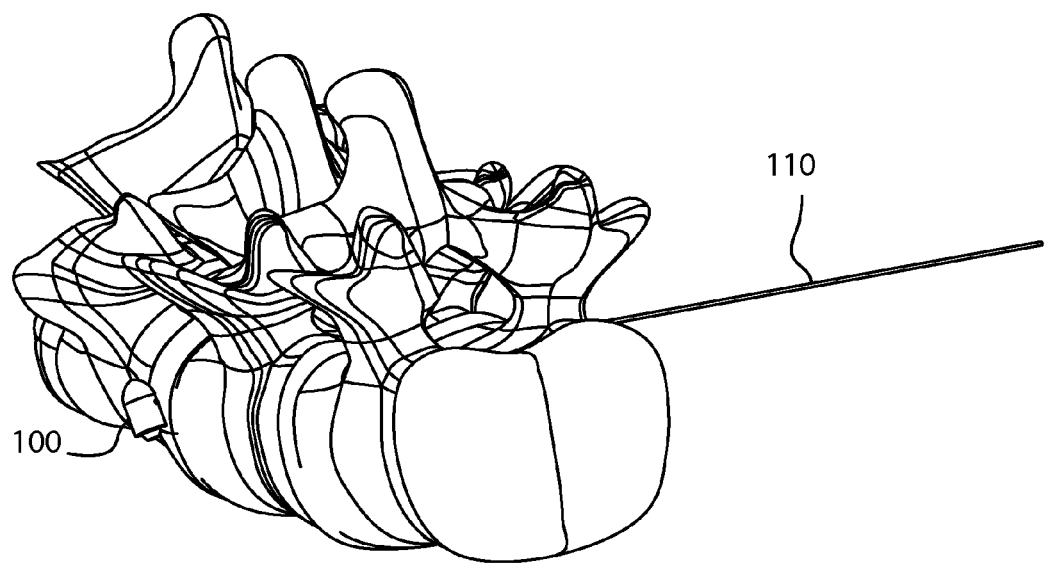
FIG. 17 is a perspective view of the anchor of FIG. 15 in a deployed configuration against the contralateral side of the disc.

Another method for placing an anchor 100 on a contralateral side 27 of the disc 26 may deploy an anchor 100 that resembles a button. This method is illustrated in FIGS. 15-17. A trephine or other coring tool (not shown) may be used to establish a pathway or hole through the annulus. An anchor 100 may be secured to an anchor inserter instrument 102. The anchor 100 may also be coupled to a portion of a guide wire 110. For example, the anchor 100 may be coupled to one end of the guide wire 110. When the anchor 100 is secured to the anchor inserter instrument 102, the guide wire 110 may rest in a central cannulation in the instrument 102. The anchor 100 may resemble a button. The anchor 100 may be elongated in one direction, so that it resembles a toggle button. The anchor 100 may move between an insertion position, in which the elongation is aligned with a center longitudinal axis of the guide wire 110, and a deployed position, in which the elongation is transverse to the axis. The anchor 100 may be described as having a smaller projected area normal to the axis in the insertion position, and a larger projected area in the deployed position. The anchor inserter instrument 102 may be aligned with the pathway or hole previously established by the coring tool. As shown in FIG. 16, the anchor 100 may be inserted into the hole and pushed across the disc space 26. When the anchor 100 is through the contralateral annulus, the anchor 100 may be deployed, or rotated, as shown in FIG. 17. For example, the anchor 100 may be deployed by pulling on the guide wire 110 or the inserter 102. The anchor 100 may disassociate from the inserter instrument 102 when the pulling force exceeds a predetermined threshold value. The inserter instrument 102 may then be removed, leaving the anchor 100 and the guide wire 110 in place, as shown in FIG. 17. In this way, the anchor 100 may be described as connecting the guide wire 110 to the disc 26. The anchor 100 may be removed when desired by sliding the inserter instrument 102 over the guide wire 110 to the anchor 100, reconnecting the instrument 102 to the anchor 100, pushing on the instrument 102 to separate the anchor 100 slightly from the contralateral annulus, pushing on the guide wire 110 to move the anchor 100 from the deployed position to the insertion position, and pulling the anchor 100 back out of the disc space 26.

Regardless of the anchor used, the guide wire 98 or 110 is thus constrained to the contralateral annulus so that cannulated instruments or additional implants may be passed over the guide wire 98, 110 with confidence that the instruments or implants will follow a safe trajectory.

Figure 18A:
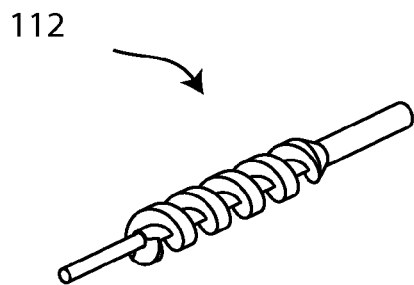
FIG. 18A is a perspective view of a portion of an auger over a guide wire.
Figure 18B:
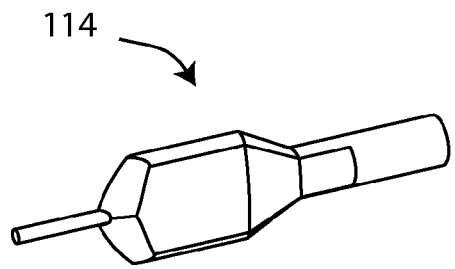
FIG. 18B is a perspective view of a portion of a paddle distractor, or spade drill, over a guide wire.
Figure 18C:
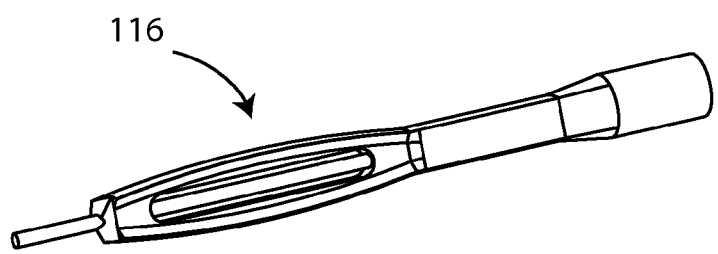
FIG. 18C is a perspective view of a portion of a shaver over a guide wire.
Figure 18D:
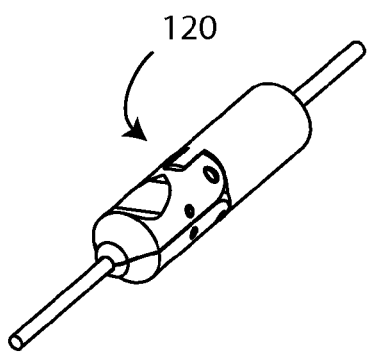
FIG. 18D is a perspective view of a portion of an expandable retrograde cutter over a guide wire.
Figure 18E:
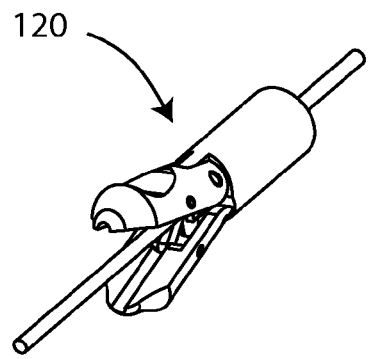
FIG. 18E is a perspective view of the cutter of FIG. 18D in an expanded configuration.

A method for performing at least a partial discectomy and/or endplate preparation may employ cannulated instruments which operate over the guide wire 98 or 110 to remove disc material and/or prepare the endplates. FIGS. 18A-18E illustrate working portions of several cannulated instruments which may be used in discectomy and/or endplate preparation. FIG. 18A shows the working portion of an auger 112 which may be rotated to simultaneously cut annulus, disc or endplate material and move the debris out of the disc space. FIG. 18B shows a paddle distractor 114 which may be inserted into the disc space 26 and rotated to provide localized distraction. Distractor 114 may also be an end cutter similar to a spade drill, and may be used in continuous rotation to cut a hole through an annulus or disc. FIG. 18C shows a shaver 116 which may be rotated in one direction or in alternating directions to cut disc or endplate material. The shaver 116 of FIG. 18C may be rigid, or it may be expandable in width transverse to the guide wire. For example, the shaver 116 may be inserted into the disc space 26 in a smaller diameter elongated configuration and expanded into a larger diameter but shorter configuration for material removal. FIGS. 18D-18E show an expandable retrograde scraper 120 which may be inserted into the disc space 26 in a closed configuration and expanded into an open configuration for material removal. The scraper 120 may be inserted into the disc space 26, opened, and pulled out to scrape and remove material. While only the working portions of the instruments have been shown in FIGS. 18A-18E, it can be appreciated that each instrument may include, for example, a shaft, a handle, or a drive fitting, such as a square drive.

After the disc space 26 and/or endplates are prepared, the contralateral anchor 88 or 100 and guide wire 98 or 110 may be removed as described above.

Figure 19:
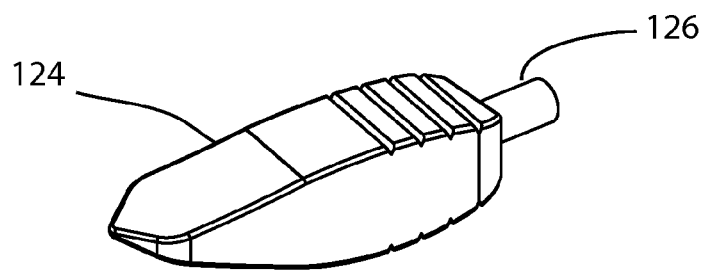
FIG. 19 is a perspective view of a trial implant and a portion of an inserter instrument shaft.
Figure 20:
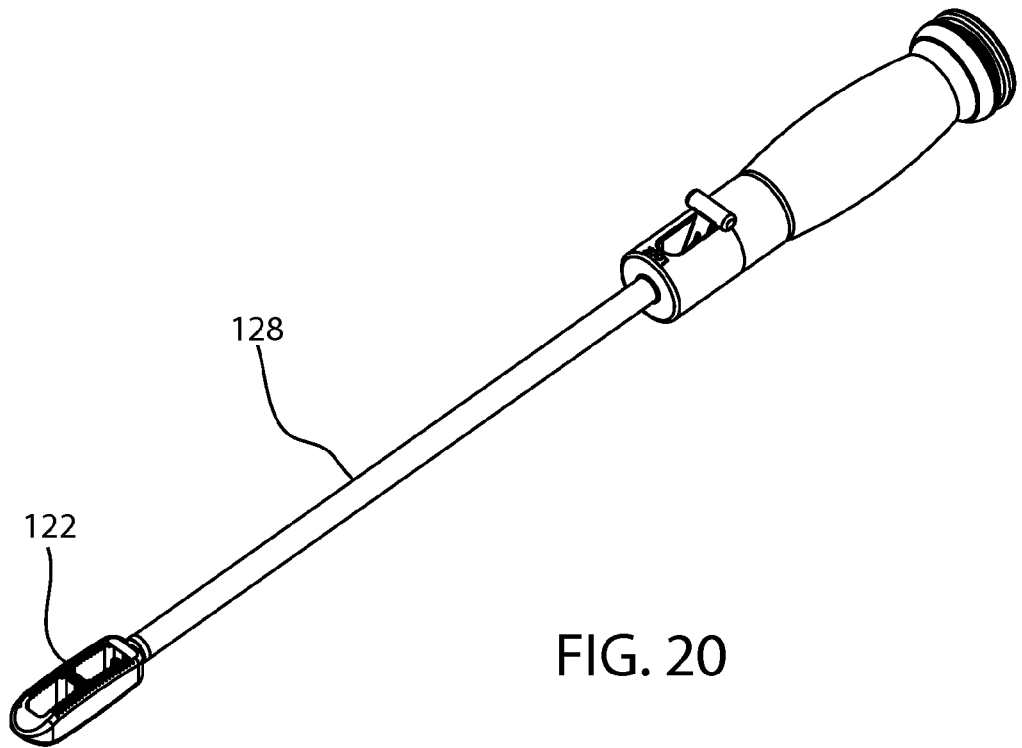
FIG. 20 is a perspective view of an implant and an inserter instrument.

A method for selecting and inserting a spinal implant 122 is illustrated in FIGS. 19-20. One or more trial implants 124 may be used in the prepared disc space 26 to establish the desired disc height or, in other words, the desired implant size. Trial implants 124 may be selected, connected to a trial implant inserter instrument 126, inserted into the disc space 26, and evaluated for fit and fill. The inserter 126 in FIG. 19 is shown in a truncated form; the complete inserter 126 may share some or all of the characteristics of inserter 128 of FIG. 20. Optionally, the trial implants 124 and trial inserter 126 may be cannulated. In this situation, the contralateral anchor 88 or 100 and guide wire 98 or 110 may remain secured to the contralateral annulus until an appropriate implant size has been established. The contralateral anchor 88 or 100 and guide wire 98 or 110 may be removed immediately prior to insertion of the implant 122. The implant 122 may be a unitary fusion cage. The implant 122 may be connected to an implant inserter instrument 128, optionally packed with bone graft material, and delivered to the prepared disc space 26. The final position of the implant 122 may be verified using fluoroscopy. When a properly sized implant 122 is positioned as desired in the disc space 26, the inserter instrument 128 may be disconnected from the implant and withdrawn along with the retractor 76 and any other remaining apparatus.

Figure 21A:
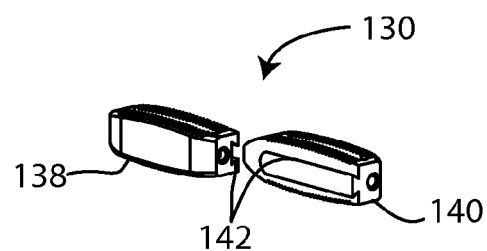
FIG. 21A is a perspective view of two portions of a segmented spinal fusion cage.
Figure 21B:
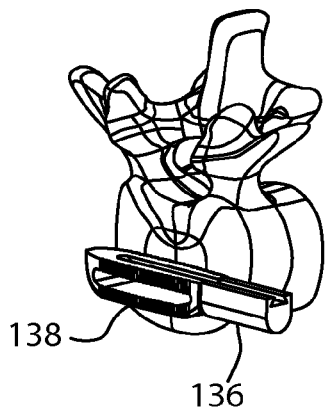
FIG. 21B is a perspective view of a first portion of the cage of FIG. 21A on a portion of an inserter shaft, with the first cage portion positioned relative to a vertebral endplate.
Figure 21C:
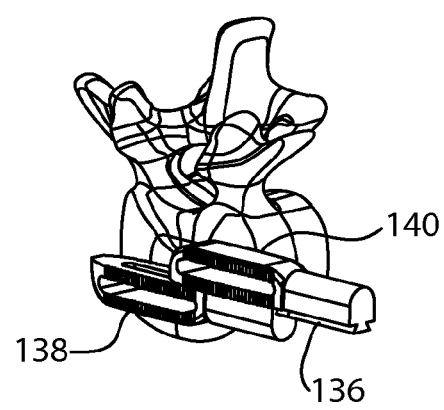
FIG. 21C is a perspective view of a second portion of the cage of FIG. 21A on a portion of another inserter shaft, with the second cage portion engaging the first cage portion.
Figure 21D:
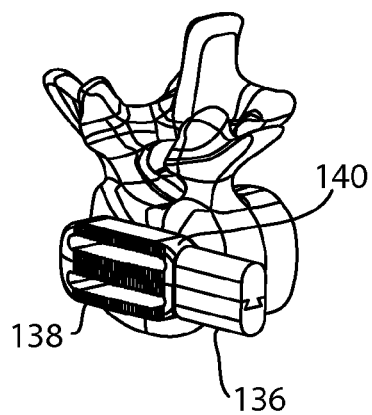
FIG. 21D is a perspective view of the first and second cage portions positioned relative to a vertebral endplate and connected to the inserter shafts.
Figure 21E:
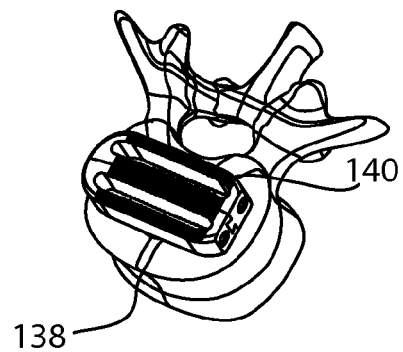
FIG. 21E is a perspective view of the first and second cage portions in their final implanted configuration.

Another method for selecting and inserting a spinal implant 130 is shown in FIGS. 21A-21E. One or more trial implants 124 may be used in the prepared disc space 26 to establish the desired disc height or, in other words, the desired implant size. Trial implants 124 may be selected, connected to a trial implant inserter instrument 126, inserted into the disc space 26, and evaluated for fit and fill. Optionally, the trial implants 124 and trial inserter 126 may be cannulated. In this situation, the contralateral anchor 88 or 100 and guide wire 98 or 110 may remain secured to the contralateral annulus until an appropriate implant size has been established. The contralateral anchor 88 or 100 and guide wire 98 or 110 may be removed immediately prior to insertion of the implant 130. The implant 130 may be a segmental fusion cage which may be inserted a piece at a time in order to minimize the insertion profile. As shown in FIG. 21A, the implant 130 may include a first portion 138 and a second portion 140 with a complementary dovetail interface 142 for sliding connection of the first and second portions 138, 140. The first portion 138 of implant 130 may be connected to an implant inserter instrument 136, optionally packed with bone graft material, and delivered to the prepared disc space 26, as shown in FIG. 21B. The inserter 136 in FIG. 21B is shown in a truncated form; the complete inserter 136 may share some or all of the characteristics of inserter 128 of FIG. 20. The second portion 140 of implant 130 may be connected to another inserter instrument 136, optionally packed with bone graft material, and slidingly connected to the first portion 138 in the prepared disc space 26, as shown in FIGS. 21C-21D. The final position of the implant 130 may be verified using fluoroscopy. When a properly sized implant 130 is positioned as desired in the disc space 26, the inserter instrument 136 may be disconnected from the implant and withdrawn along with the retractor 76 and any other remaining apparatus. The complete implant 130 is shown in FIG. 21E.

The present invention may be embodied in other specific forms without departing from its spirit or essential characteristics. It is appreciated that various features of the above-described examples can be mixed and matched to form a variety of other alternatives. It is also appreciated that this system is not limited to spinal surgery; it may be used for surgical approaches to other body structures or in other directions. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for spine surgery, wherein the method comprises:
   securing an anchor to an anchor inserter instrument;
   coupling the anchor to a first portion of a guide wire;
   inserting the anchor and the first portion of the guide wire through a second side of an intervertebral disc of a patient with the anchor inserter instrument;
   passing the anchor and the first portion of the guide wire through the disc to a first side of the disc opposite the second side of the disc with the anchor inserter instrument;
   connecting the first portion of the guide wire to the first side of the disc with the anchor so that the guide wire extends through the second side of the disc and outside the patient;
   removing the anchor inserter instrument, leaving the anchor and the guide wire in place relative to the disc;
   sliding a cannulated instrument over the guide wire to the disc; and
   removing material from at least one of the disc and a vertebra adjacent to the disc with the cannulated instrument.

2. The method of claim 1, wherein connecting the first portion of the guide wire to the first side of the disc with the anchor comprises releasably connecting the anchor to an annulus of the disc.

3. The method of claim 1, wherein connecting the first portion of the guide wire to the first side of the disc with the anchor comprises releasably connecting the anchor to the first side of the disc.

4. The method of claim 3, wherein connecting the first portion of the guide wire to the first side of the disc with the anchor comprises moving the anchor between an insertion configuration and a deployed configuration, wherein the anchor has a larger projected area in the deployed configuration than in the insertion configuration, wherein the projected area is normal to a center longitudinal axis of the guide wire.

5. The method of claim 4, wherein moving the anchor between the insertion configuration and the deployed configuration comprises pulling on the guide wire to rotate at least a portion of the anchor.

6. The method of claim 1, wherein the cannulated instrument is selected from the group consisting of an annulotomy instrument, a discectomy instrument, a vertebral endplate preparation instrument, an inserter instrument, and a drill.

7. The method of claim 1, comprising:
   sliding the cannulated instrument over the guide wire into the disc; and
   moving the cannulated instrument over the guide wire within the disc, wherein the movement of the cannulated instrument is selected from the group consisting of translation along a center longitudinal axis of the guide wire, rotation around the axis, and translation normal to the axis.

8. The method of claim 1, comprising:
   removing the anchor and the guide wire by sliding the anchor inserter instrument over the guide wire to the anchor, re-securing the anchor to the anchor inserter instrument, disconnecting the anchor and the first portion of the guide wire from the first side of the disc, and passing the anchor and the first portion of the guide wire through the second side of the disc and outside the patient.

9. A method for spine surgery, wherein the method comprises:
   securing an anchor to an anchor inserter instrument;
   coupling the anchor to a first portion of a guide wire;
   connecting the anchor and the first portion of the guide wire to a first side of an intervertebral disc of a patient with the anchor inserter instrument;
   extending the guide wire from the first side of the intervertebral disc through a second side of the intervertebral disc to a position outside the patient, wherein the second side of the intervertebral disc is opposite the first side of the intervertebral disc, wherein a second portion of the guide wire is outside the patient;
   removing the anchor inserter instrument, leaving the anchor and the guide wire in place relative to the disc;
   inserting the second portion of the guide wire into a cannulation in a second instrument;
   sliding the second instrument along the guide wire to the intervertebral disc; and
   cutting at least one of an annulus, an intervertebral disc, and a vertebra with the second instrument.

10. The method of claim 9, wherein connecting the first portion of the guide wire to the first side of the intervertebral disc with the anchor comprises connecting the anchor to an annulus of the intervertebral disc.

11. The method of claim 10, wherein connecting the anchor to the annulus of the intervertebral disc comprises moving the anchor between an insertion configuration and a deployed configuration, wherein the anchor has a larger projected area in the deployed configuration than in the insertion configuration, wherein the projected area is normal to a center longitudinal axis of the guide wire.

12. The method of claim 11, wherein moving the anchor between the insertion configuration and the deployed configuration comprises pulling on the guide wire to rotate at least a portion of the anchor.

13. The method of claim 9, wherein the instrument is selected from the group consisting of an annulotomy instrument, a discectomy instrument, a vertebral endplate preparation instrument, an inserter instrument, and a drill.

14. The method of claim 9, comprising:
   sliding the instrument along the guide wire into the intervertebral disc; and
   moving the instrument over the guide wire within the intervertebral disc, wherein the movement of the instrument is selected from the group consisting of translation along a center longitudinal axis of the guide wire, rotation around the axis, and translation normal to the axis.

15. The method of claim 9, comprising:
   removing the anchor and the guide wire by sliding the anchor inserter instrument over the guide wire to the anchor, re-securing the anchor to the anchor inserter instrument, disconnecting the anchor and the first portion of the guide wire from the first side of the intervertebral disc, and passing the anchor and the first portion of the guide wire through the second side of the intervertebral disc and outside the patient.

* * * * *